(12) United States Patent
Carlisle et al.

(10) Patent No.: US 7,232,430 B2
(45) Date of Patent: Jun. 19, 2007

(54) AIR-IN-LINE AND PRESSURE DETECTION

(75) Inventors: Jeffrey A. Carlisle, Salsbury, MA (US);
Keena B. Patel, N. Andover, MA (US)

(73) Assignee: Mack Ventures, Inc., Arlington, VT (US)

( * ) Notice: Subject to any disclaimer, the term of this patent is extended or adjusted under 35 U.S.C. 154(b) by 1051 days.

(21) Appl. No.: 09/899,300

(22) Filed: Jul. 6, 2001

(65) Prior Publication Data
US 2002/0004645 A1 Jan. 10, 2002

Related U.S. Application Data

(60) Provisional application No. 60/216,772, filed on Jul. 7, 2000.

(51) Int. Cl.
*A61M 31/00* (2006.01)

(52) U.S. Cl. .................................... 604/500

(58) Field of Classification Search ............. 604/65, 604/131, 66, 154, 67, 156, 30, 134, 31, 135, 604/32, 122, 48, 500; 128/DIG. 12, 13
See application file for complete search history.

(56) References Cited

U.S. PATENT DOCUMENTS

| 4,526,574 A | | 7/1985 | Pekkarinen |
| 4,846,792 A | | 7/1989 | Bobo et al. |
| 4,919,596 A | * | 4/1990 | Slate et al. ................. 417/18 |
| 4,923,444 A | | 5/1990 | Daoud et al. |
| 4,927,411 A | * | 5/1990 | Pastrone et al. ............ 604/65 |
| 4,959,050 A | | 9/1990 | Bobo |
| 4,979,940 A | | 12/1990 | Bobo et al. |
| 4,981,467 A | | 1/1991 | Bobo et al. |
| 5,190,522 A | | 3/1993 | Wojcicki et al. |
| 5,205,819 A | | 4/1993 | Ross et al. |
| 5,554,115 A | | 9/1996 | Thomas et al. |
| 5,616,124 A | | 4/1997 | Hague et al. |
| 5,643,212 A | | 7/1997 | Coutré et al. |
| 5,695,473 A | * | 12/1997 | Olsen ....................... 604/153 |
| 5,713,865 A | | 2/1998 | Manning et al. |
| 5,718,569 A | | 2/1998 | Holst |
| 5,904,666 A | | 5/1999 | DeDecker et al. |
| 5,906,589 A | | 5/1999 | Gordon et al. |
| 5,935,106 A | * | 8/1999 | Olsen ....................... 604/153 |

OTHER PUBLICATIONS

Devita, Vincent T., Jr. et al., *Biologic Therapy of Cancer*, 2nd Edition, c1995, Philadelphia, J.B. Lippincott Company, pp. 53-86.
Fagerberg, Jan et al., "Humoral anti-idiotypic and anti-anti-idiotypic . . . ," Cancer Immunol Immunother, 1996, 42, pp. 81-87.

(Continued)

*Primary Examiner*—Manuel Mendez
(74) *Attorney, Agent, or Firm*—Heslin Rothenberg Farley & Mesiti P.C.

(57) ABSTRACT

Methods and apparatus for air content and pressure measurement of sample fluid, especially sample fluid in association with an infusion pump. Volume change in a chamber as the chamber transitions between negative and positive pressure relates to the air content in the chamber. In particular, in an infusion pump, the volume change of infusion fluid as it transitions between being under negative pressure and positive pressure within a cassette central chamber, e.g., pumping chamber, relates to the air content in the infusion fluid. The outlet pressure of the cassette central chamber, e.g., blood pressure, can be monitored based on the cassette central chamber pressure.

38 Claims, 4 Drawing Sheets

OTHER PUBLICATIONS

Benchimol, Sarita et al., "Carcinoembryonic antigen, a human tumor . . . ," Cell, vol. 57, Apr. 21, 1989, pp. 327-334P.

Litvinov, Sergey V. et al., "Ep-cam: a human epithelial antigen . . . ," The Journal of Cell Biology, vol. 125, 1994, pp. 437-446.

Miyake, Masayuki et al., "Correlation of expression . . . ," The New England Journal of Medicine, vol. 327, No. 1, pp. 14-18.

Koprowski, Hilary et al., "Human anti-idiotype antibodies . . . ," Proc. Natl. Acad. Sci., vol. 81, Jan. 1984, pp. 216-219.

Rao, Yong et al., "Indentification of a peptide sequence . . . ," The Journal of Cell Biology, vol. 118, No. 4, Aug. 1992, pp. 937-949.

Zola, Heddy et al., *Monoclonal Antibodies a Manual of Techniques*, CRC Pres, c1987, Boca Raton, FL., pp. 23-61.

* cited by examiner

AIR-IN-LINE AND PRESSURE DETECTION

This application is based on and claims priority from U.S. Provisional Patent Application No. 60/216,772, filed Jul. 7, 2000.

FIELD OF THE INVENTION

The present invention relates to a system and methods of determining air content and pressure in fluid, especially in association with an infusion pump.

BACKGROUND OF THE INVENTION

There is a need in the field for methods of measuring air content and pressure of a sample fluid. Particularly in an infusion pump, it is critical to determine the air content of the infusion fluid and the fluid pressure down stream of the outlet valve of the infusion pump.

SUMMARY OF THE INVENTION

The present invention is directed in part to unique methods of content measurement of a sample fluid. The present invention is based on the discovery that volume change in a chamber, as the chamber transitions between negative and positive pressure relates to the air content in the chamber. In particular, in an infusion pump, the volume change of infusion fluid as it transitions between being under negative pressure and positive pressure within a cassette central chamber, e.g., pumping chamber, relates to the air content in the infusion fluid. In addition, the present invention provides methods for determining pressure of a sample fluid.

BRIEF DESCRIPTION OF THE DRAWINGS

These and other objects and advantages of the invention will become more apparent and more readily appreciated from the following detailed description of an exemplary embodiment of the invention taken in combination with the accompanying drawings, of which.

DETAILED DESCRIPTION

Infusion pumps are widely used for administering medications to patients over an extended time period. During an infusion of medication, it is critical to monitor the air content of the fluid medication administered to a patient. In addition, it is often convenient/helpful to measure the pressure on the patient side of the pump, e.g. measure the blood pressure of the patient. One of the applications of the methods for air content measurement of a sample fluid is to measure the air content in a cassette central chamber in an infusion pump. In addition, the mechanism for air content measurement also provides means to monitor the blood pressure of a patient connected to an infusion pump.

Figure 1:
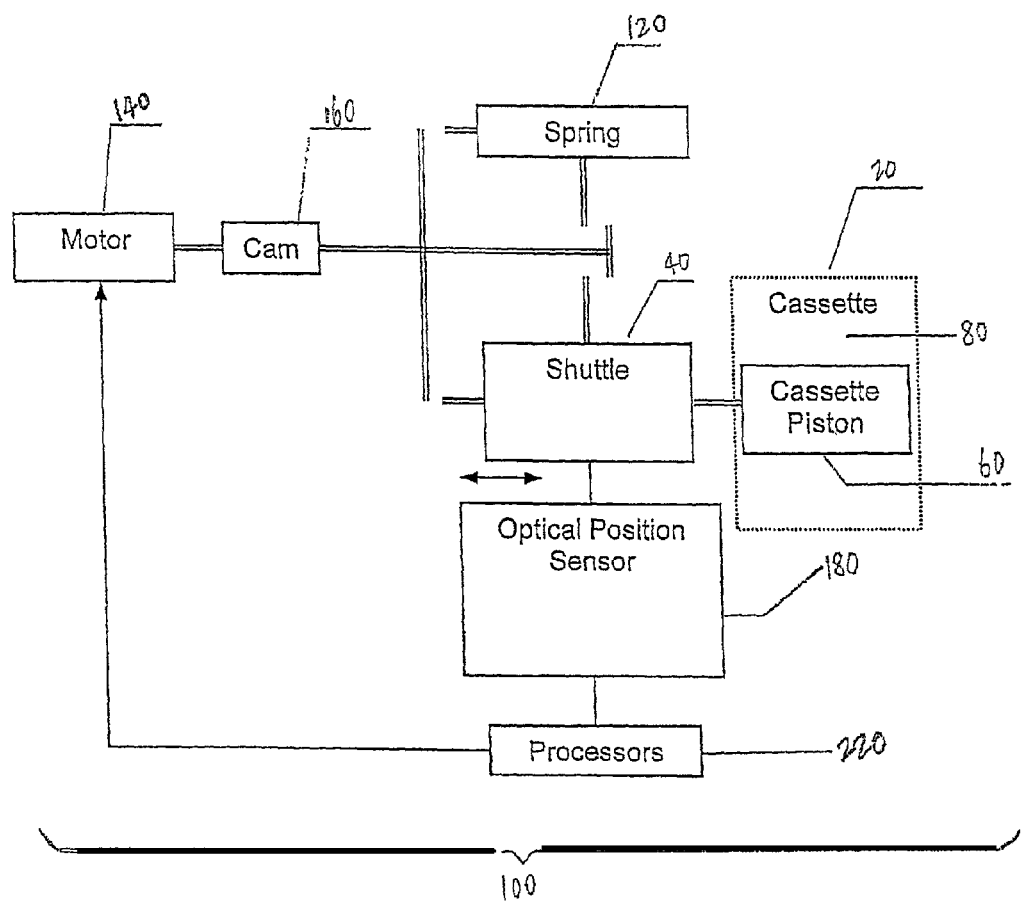
FIG. 1 is a block diagram illustrating the fluid delivery system topology of an infusion pump.

FIG. 1 is a block diagram illustrating one embodiment of the present invention. The fluid delivery system 100 includes a cassette assembly 20 and a shuttle mechanism 40. A suitable cassette assembly is described in patent application Ser. No. 60/216,658, filed Jul. 7, 2000, entitled "Cassette", to Carlisle, Costa, Holmes, Kirkman, Thompson and Semler, the entire contents of which are incorporated herein by reference. Within the cassette assembly 20 is a cassette piston 60 and a cassette central chamber 80. A spring 120 biases shuttle mechanism 40 which is connected to the cassette piston 60. Piston 60 slides freely in the cassette central chamber 80 to draw fluid into central chamber 80 and pump fluid out of central chamber 80. A motor 140 is activated in one direction to draw the cassette piston 60 out of cassette central chamber 80 via cam 160 and shuttle 40. When the cassette piston 60 is fully withdrawn, shuttle 40 disengages from cam 160 and motor 140, so that spring 120 pushes the cassette piston 60 into the cassette central chamber 80 via shuttle 40 to apply positive pressure to the fluid in the cassette central chamber 80. The shuttle mechanism 40 is also operably linked to an optical position sensor 180. A suitable position sensor is described in patent application Ser. No. 60/217,885, filed Jul. 7, 2000, entitled "Optical Position Sensor and Position Determination Method", to Carlisle, Kaplan and Kirkman, the entire contents of which are incorporated herein by reference. A processor 220 is connected to motor 140 and the position sensor 180.

Figure 2:
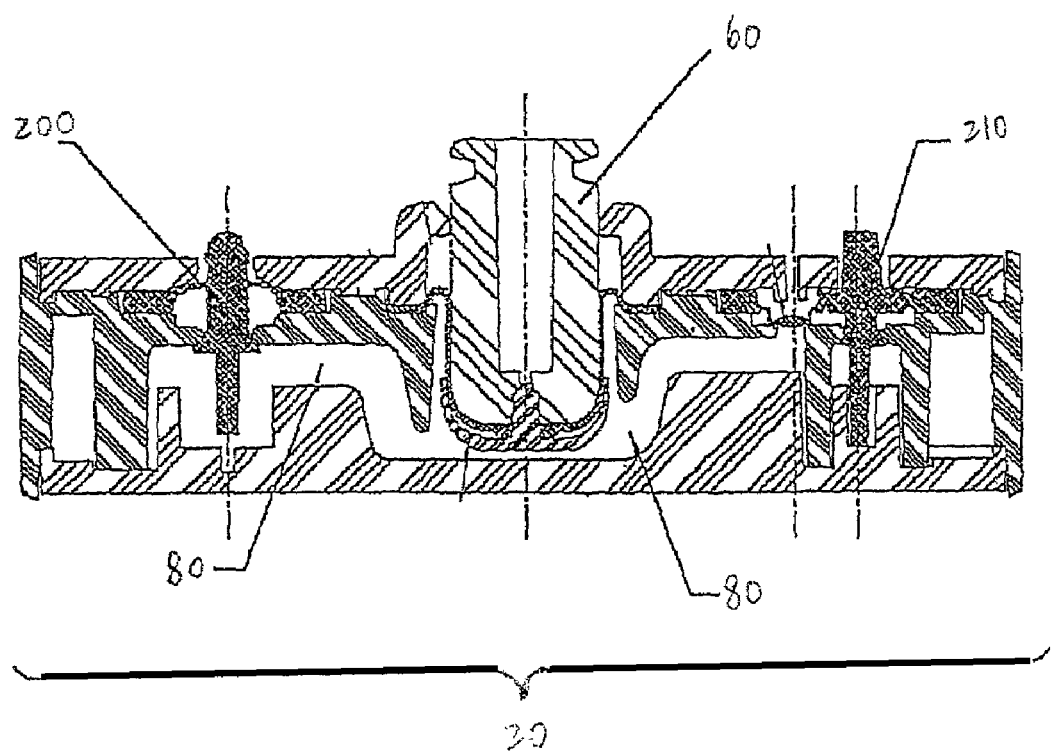
FIG. 2 is a block diagram illustrating a cross-sectional view of the cassette assembly of an infusion pump.

FIG. 2 is a diagram illustrating a cross-sectional view of a cassette assembly 20. The cassette assembly 20 contains an inlet valve 200, an outlet valve 210, a cassette central chamber 80, and a cassette piston 60. Cassette piston 60 is connected to shuttle 40.

In operation, the motor 140 is activated in one direction to withdraw the cassette piston 60 against the force of spring 120 via cam 160, creating a relative vacuum in the cassette central chamber 80 and pulling fluid through a one-way passive inlet valve 200 into the cassette central chamber 80. During this fill stroke, the pressure in the cassette central chamber 80 is negative, e.g., between 0 and −10 psi. The amount of negative pressure depends on the withdrawal speed of the piston, fluid resistance, fluid viscosity, etc. Once the cassette piston 60 has been withdrawn, cam 160 disengages from the shuttle 40, enabling the spring mechanism 120 to urge shuttle 40 to drive piston 60 into the cassette central chamber 80. The pressure in the chamber then moves from a negative value through zero to a positive value. The one-way passive inlet valve 200 is now fully closed. The positive pressure in the cassette central chamber 80 is typically between +2 and +7 psi depending on the spring force applied to the cassette piston 60 through the shuttle 40 which is directly related to the length of the withdrawal stroke, e.g., the further the withdrawal stroke the stronger the spring force.

Figure 3:
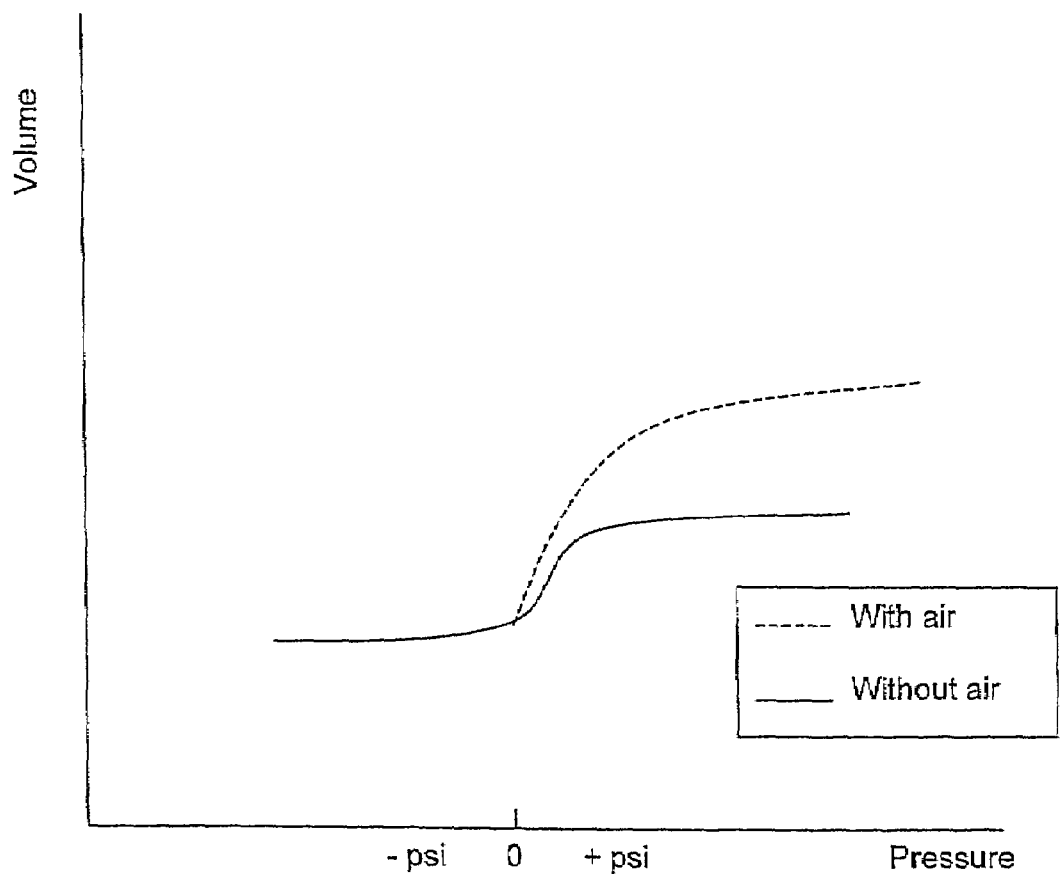
FIG. 3 illustrates changes in cassette central chamber volume as a function of pressure.

In a closed cassette central chamber, the volume changes as a function of cassette central chamber pressure. In theory, when the cassette central chamber 80 is closed and contains only liquid, i.e., air free fluid, the cassette central chamber is not compressible, thus no volume change occurs. Nevertheless in practice, a "base volume change" exists when the chamber contains just air free fluid (as shown in FIG. 3). Such "base volume change" is irrelevant to the air content in the fluid and is mostly due to system designs such as the shape of a sealing member of the cassette piston 60 or the flexing of elastomeric inlet and outlet valve elements connected to the cassette central chamber 80.

For example, the cassette piston 60 in the cassette central chamber 80 acts as a nearly ideal piston when under positive pressure from the spring mechanism 120; thus a change in the axial position of the piston represents a fluid volume change in the cassette central chamber. Nevertheless, when cassette central chamber pressure changes from negative to positive, the shape of a sealing member of the cassette piston changes and results in piston travel without any change in central chamber fluid volume. This amount of travel contributes to the "base volume change"; it is significant, however, that this travel is a relative constant of the system design and does not change over time. In addition, the elastomeric valve elements connected to the cassette central chamber have some inherent displacement determined by their geometry and material properties. When under pressure, these elements move and to an insignificant degree, continue to move (creep) over time. The movement of these elements also contributes to the "base volume change".

Figure 4:
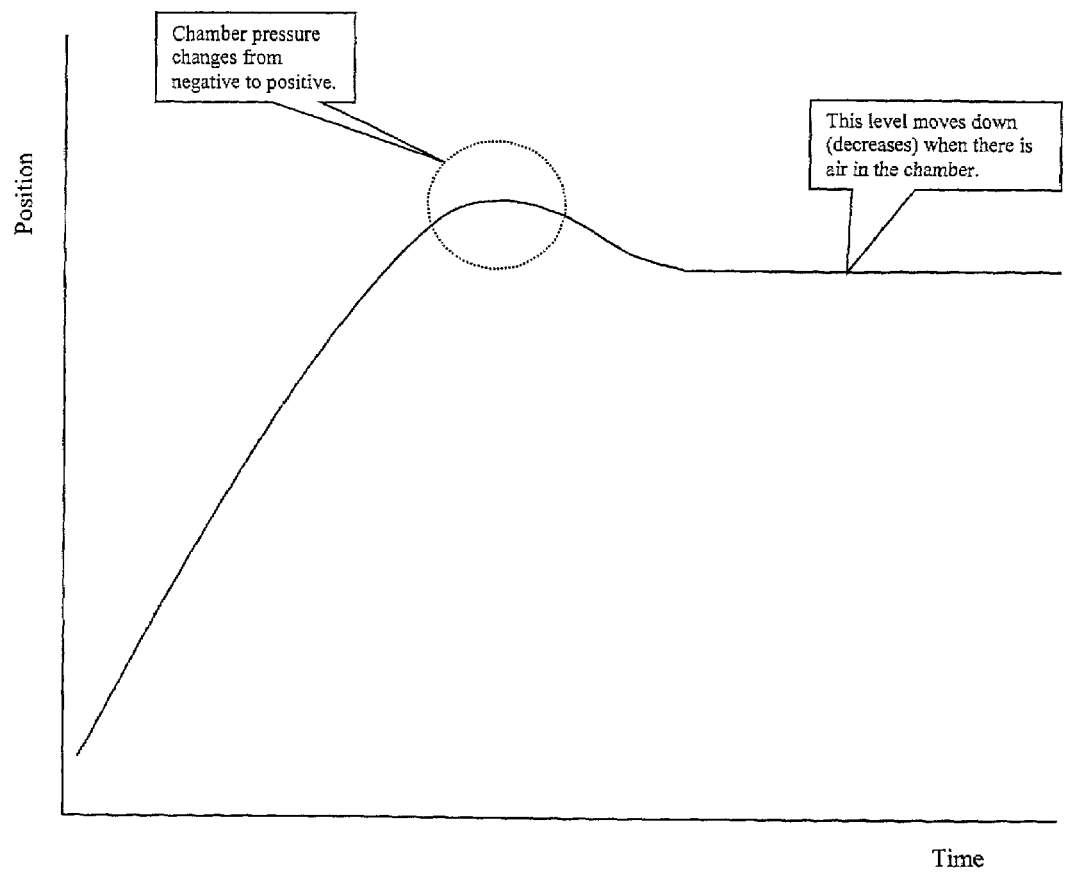
FIG. 4 illustrates changes in piston position as a function of time.

The "base volume change" of the cassette central chamber 80 can be determined by detecting the volume change of a control fluid under the pressure change of the cassette central chamber. The volume change can be measured by determining the change of shuttle position, i.e., the piston travel position when the cassette central chamber pressure changes from negative to positive. The change of shuttle position is determined by the precision position sensor 180 linked to the shuttle mechanism 60. For example, one can compare the shuttle position in two states: the peak position during piston withdrawal and the shuttle position after the spring pressure is applied (as shown in FIG. 4). This net displacement change of the shuttle position as a result of the pressure change in the cassette central chamber 80 filled with control fluid is a measure of the "base volume change" of the system 100, e.g., the volume change that is inherent in the system 100.

In one embodiment, the "base volume change" of a control fluid is determined more than once and statistically conservative limits of "base volume change", e.g., lower than average, is selected as the "base volume change" for calculating the fluid air content. In another embodiment, the base volume change of a control fluid for a sample infusion fluid is determined by measuring the median volume change of more than one sample of the same infusion fluid, e.g., over more than one fill stroke, resulting from the pressure change of the cassette central chamber. In yet another embodiment, the base volume change is the median volume change of an infusion fluid over eleven (11) contiguous fill strokes, and is updated or modified periodically throughout an infusion therapy; and such base volume change is used to measure the sample fluid air content of the same infusion fluid.

In a closed cassette central chamber, e.g., both inlet and outlet valves are closed, any cassette central chamber volume-versus-pressure changes above the "base volume change" are interpreted as volume changes in the cassette central chamber due to the presence of air (as shown in FIG. 3). The air content of fluid contributes to the total volume change of the cassette central chamber and is proportional to the total volume change, e.g., sample volume change minus the base volume change.

For example, one can fill the cassette central chamber 80 with a sample fluid until the volume (gVolMax) in the chamber is greater than the desired volume of fluid to be delivered in a single pump stroke (gvdue) plus the "base volume change" (Vbase). During the fill cycle, the fill volume can be monitored through the piston position, i.e., the shuttle position which is determined by the optical position sensor 180. As a result of the geometry and design of the cassette assembly 20, there is a linear relationship between the shuttle position and the fill volume. Once the fill volume (gVolMax) is achieved, the motor direction is reversed so that the shuttle 40 falls off the cam 160 and rides freely on the spring mechanism 120. Similarly the end-diastolic volume (gVolEnd) can be determined from the stabilized shuttle position alter the cam 160 releases shuttle 40. The sample volume change is the difference between the gVolMax and gVolEnd. The air content of the sample fluid is calculated in processor 220 as follows:

Air content (Volair)~Sample volume change–Base volume change

~(gVolmax-gVolEnd)–Base volume change

The air content measured according to the present invention is independent of the size and shape of the air bubble contained in a sample fluid, e.g., the air content includes the content of big bubbles, small bubbles, integrated bubbles, and unintegrated bubbles.

In one embodiment, the effective amount of fluid that is pumped out of cassette central chamber 80 is calculated based on the air content of a sample fluid. For example, for a given stroke, the effective amount of fluid that is infused is calculated in processor 220 as follows:

effective amount of fluid infused~gvolmax–Volair

In another embodiment, the proportion of air content and volume content in a given stroke is calculated directly on the change of position of the piston. Specifically the proportion is calculated in processor 220 as follows:

proportion of air/fluid content=(position change due to pressure change)/(max. position under neg. pressure)

The processor 220 adjusts subsequent fluid flow rate based on the air/fluid content proportion in a given stroke to compensation for the air content detected in a sample fluid.

In yet another embodiment, processor 220 compares the air content of a sample fluid to a predetermined value stored in the processor 220; the processor 220 activates an alarming device if the air content of the sample fluid is close to or beyond the predetermined value. Alternatively, the processor 220 activates an alarming device as well as shuts down the out flow of sample fluid from the cassette central chamber 80, e.g., closes the outlet valve 210 of the cassette central chamber 80 and shuts down infusion process by the fluid delivery system 100.

According to another feature of the invention, sample fluid continuously passes through cassette central chamber 80 and the air content of the sample fluid is determined at different time points and stored in processor 220. The processor 220 calculates accumulated air content of the sample fluid by adding the air content values collected at different time points. Such accumulated air content over a period of time is compared to a threshold air content value stored in the processor 220; the processor 220 triggers a notifying device, e.g., an alarm, if the accumulated air content is close or beyond a predetermined limitation. Alternatively, the processor 220 activates a notifying device as well as shuts down the out flow of sample fluid from the cassette central chamber 80, e.g., closes the outlet valve 210 of the cassette central chamber 80 and shuts down infusion process by the fluid delivery system 100.

In one embodiment, the outlet pressure of the cassette central chamber, e.g., the blood pressure of a mammal such as a human connected to the infusion pump is monitored. For example, during the fluid displacement, the outlet valve 210 of the cassette central chamber 80 is opened via external actuation. Fluid then flows from the higher pressure in the cassette central chamber 80 to the outlet via the outlet valve 210. If the outlet valve 210 remains open, the cassette piston 60 will stop when the cassette central chamber pressure equals the outlet pressure. The position of the piston on the spring load is associated with a known spring force. Processor 220 then calculates the outlet pressure from the fixed geometry of the cassette central chamber 80. With the outlet valve 210 open, the outlet pressure including even rapid changes in arterial, vein, or capillary pressure of a patient can be measured.

For example, the spring rate, k (in units of force/distance), of the shuttle mechanism 40 and the piston cross-sectional area, A, are known system design constants. Such system design constants, i.e., k/A are pre-calculated and stored in the processor 220 as Design Constant. During the empty cycle, the outlet valve 210 of the cassette central chamber remains open. Once the spring 120 reaches a stabilized position, the system reaches equilibrium, e.g., the outlet pressure equals the cassette central chamber pressure. Subsequently the shuttle position, i.e., X, is measured by the optical position sensor 180 and processor 220 calculates the outlet pressure as the following:

Outlet pressure=Design_Constant*X

In another embodiment, processor 220 monitors the outlet pressure of the cassette central chamber and compares it to a predetermined value over a period of time. An increase of the outlet pressure indicates a partial or complete blockage of the cassette central chamber outlet, i.e., blockage of the outlet pathway or a body fluid pathway receiving fluid displaced from the cassette central chamber 80. Depending on the degree of outlet pressure increase, processor 220 generates a signal to either alert the pressure increase or stop the fluid displacement of the system 100.

OTHER EMBODIMENTS

Although several exemplary embodiments of this invention have been described in detail above, those skilled in the art will readily appreciate that many modifications are possible in the exemplary embodiment without materially departing from the novel teachings and advantages of this invention. Accordingly, all such modifications are intended to be included within the scope of this invention as defined in the following claims.

What is claimed is:

1. A method of determining pressure of a sample fluid comprising:
   connecting the sample fluid to a chamber, wherein the chamber has an inlet valve, an outlet valve, and an assembly connected to a pressure source which pumps a chamber fluid out of the chamber, and wherein the sample fluid is connected to the chamber fluid through the outlet valve; and
   determining chamber pressure when the pressure of the sample fluid equals the chamber pressure.

2. The method of claim 1, wherein the sample fluid is a body fluid of a mammal.

3. The method of claim 2, wherein the body fluid is blood.

4. The method of claim 2, wherein the body fluid is blood in a vessel selected from the group consisting of artery, vein, and capillary.

5. The method of claim 2, wherein the mammal is a human.

6. The method of claim 1, wherein the chamber is part of an infusion pump.

7. The method of claim 6, wherein the chamber fluid is an infusion fluid.

8. The method of claim 1, wherein the inlet valve of the chamber is closed when the pressure source pushes the chamber fluid out of the chamber.

9. The method of claim 1, wherein the assembly comprises a cassette piston.

10. The method of claim 9, wherein the determination of the chamber pressure includes determining position of the piston.

11. The method of claim 1, wherein the pressure source comprises a motor which generates a negative pressure in the chamber and pumps the chamber fluid into the chamber, and a spring which generates a positive pressure and pumps the chamber fluid out of the chamber.

12. The method of claim 11, wherein the determination of the position of the piston includes using an optical position sensor.

13. The method of claim 1 further comprising monitoring the pressure of the sample fluid including determining the pressure of the sample fluid at more than one time point over a period of time.

14. The method of claim 1 further comprising comparing the pressure of the sample fluid to a predetermined value.

15. An apparatus for monitoring pressure of a sample fluid comprising:
   a central chamber with an inlet valve and an outlet valve, wherein a sample fluid is connected to a chamber fluid in the central chamber through the outlet valve.
   an assembly moving in and out of the central chamber;
   a pressure source connected to the assembly, and wherein the pressure source comprises a motor which generates a negative pressure in the central chamber and pumps fluid into the central chamber via the assembly, and a spring which generates a positive pressure in the central chamber and pumps fluid out of the central chamber via the assembly;
   a position sensor connected to the assembly, wherein the position sensor determines a position change of the assembly; and
   a processor connected to the position sensor, wherein the processor receives the position change of the assembly and calculates pressure of the central chamber when the pressure of the sample fluid equals the pressure of the central chamber.

16. The apparatus of claim 15, wherein the processor further compares the pressure of the sample fluid to a predetermined value.

17. The apparatus of claim 16 further comprising an alarming device connected to the processor, wherein the processor activates the alarming device when the pressure of the sample fluid equals or is beyond the predetermined value.

18. The apparatus of claim 16, wherein the processor prevents the fluid from leaving the central chamber when the pressure of the sample fluid equals or is beyond the predetermined value.

19. The apparatus of claim 18, wherein the processor closes the outlet valve and turns off the motor when the pressure of the sample fluid equals or is beyond the predetermined value.

20. The apparatus of claim 15 wherein the sample fluid is a body fluid of a mammal.

21. The apparatus of claim 20 wherein the body fluid is blood.

22. The apparatus of claim 20 wherein the body fluid is blood in a vessel selected from the group consisting of artery, vein, and capillary.

23. The apparatus of claim 15 wherein the chamber is part of an infusion pump.

24. The apparatus of claim 23 wherein the chamber fluid is an infusion fluid.

25. A method of determining pressure of a sample fluid comprising:
- connecting the sample fluid to a chamber, wherein the chamber has an inlet valve, an outlet valve, and an assembly connected to a pressure source which assembly is operable to pump a chamber fluid out of the chamber, and wherein the sample fluid is connected to the chamber fluid through the outlet valve;
- operating the assembly to pump chamber fluid out of the chamber through the outlet valve until the chamber pressure equals the pressure of the sample fluid; and
- determining chamber pressure when the pressure of the sample fluid equals the chamber pressure.

26. The method of claim 25, wherein the sample fluid is a body fluid of a mammal.

27. The method of claim 26, wherein the body fluid is blood.

28. The method of claim 26, wherein the body fluid is blood in a vessel selected from the group consisting of artery, vein, and capillary.

29. The method of claim 26, wherein the mammal is a human.

30. The method of claim 25, wherein the chamber is part of an infusion pump.

31. The method of claim 30, wherein the chamber fluid is an infusion fluid.

32. The method of claim 25, wherein the inlet valve of the chamber is closed when the assembly is operated to pump chamber fluid out of the chamber.

33. The method of claim 25, wherein the assembly comprises a cassette piston.

34. The method of claim 33, wherein the determination of the chamber pressure includes determining position of the piston.

35. The method of claim 25, wherein the pressure source comprises a motor which generates a negative pressure in the chamber and pumps the chamber fluid into the chamber, and a spring which generates a positive pressure and pumps the chamber fluid out of the chamber.

36. The method of claim 35, wherein the determination of the position of the piston includes using an optical position sensor.

37. The method of claim 25 further comprising monitoring the pressure of the sample fluid including determining the pressure of the sample fluid at more than one time point over a period of time.

38. The method of claim 25 further comprising comparing the pressure of the sample fluid to a predetermined value.

* * * * *